United States Patent [19]

Dietzen

[11] Patent Number: 5,795,789
[45] Date of Patent: Aug. 18, 1998

[54] STANDARD SOLUTION FOR THE DETERMINATION OF THYROID FUNCTION

[75] Inventor: Dennis Jerome Dietzen, Bear, Del.

[73] Assignee: Dade Behring Inc., Deerfield, Ill.

[21] Appl. No.: 868,528

[22] Filed: Jun. 4, 1997

[51] Int. Cl.$^6$ .......................... G01N 33/53; G01N 31/00
[52] U.S. Cl. .................. 436/500; 436/8; 436/16; 435/4; 435/967
[58] Field of Search .................. 435/4, 967, 7.9; 436/8, 15, 16, 500

[56] References Cited

U.S. PATENT DOCUMENTS

| | | | |
|---|---|---|---|
| 5,142,010 | 8/1992 | Olstein | 526/248 |
| 5,283,005 | 2/1994 | Nelson, Jr. et al. | 252/380 |
| 5,342,788 | 8/1994 | Kunst et al. | 436/500 |
| 5,576,219 | 11/1996 | Bienhaus et al. | 436/500 |

OTHER PUBLICATIONS

J.B. Henry, editor, Clinical Diagnosis and Management by Laboratory Methods, W.B. Saunders Company, Philadelphia, 16th edition p. 422, 1979.

Sigma Chemical Company 1993 Biochemicals Organic Compounds and Diagnostic Reagents Catalog pp. 64 and 2073.

Sigma Chemical Company 1994 Diagnostics Catalog p. 166.

*Primary Examiner*—Carol A. Spiegel
*Attorney, Agent, or Firm*—Leland K. Jordan

[57] ABSTRACT

A stabilized liquid standard solution for use in calibrating assays of thyroid function containing albumin and known amounts of at least two analytes selected from a group consisting of total thyroxine, free thyroxine, total triiodothyronine, and free triiodothyronine, and optionally, thyroid stimulating hormone.

12 Claims, 7 Drawing Sheets

STANDARD SOLUTION FOR THE DETERMINATION OF THYROID FUNCTION

FIELD OF THE INVENTION

This invention relates to standard solutions containing protein, buffer, stabilizers and analytes adjusted to specific levels for calibration of chemical analyzers. In particular, this invention relates to a stabilized standard solution for the calibration of clinical assays useful in assessing thyroid function, including total thyroxine, unbound thyroxine, total triiodothyronine, unbound triiodothyronine, and thyroid stimulating hormone.

BACKGROUND OF THE INVENTION

The thyroid gland is an endocrine gland located within the neck which synthesizes thyroxine ($T_4$) and also small amounts of triiodothyronine ($T_3$) by incorporation of inorganic iodide into tyrosine residues of thyroglobulin. $T_4$ is the principal circulating thyroid hormone but its effects are mediated after intracellular conversion to $T_3$. $T_4$ and $T_3$ circulate in the blood predominantly bound (>99%) to the serum proteins thyroxine binding globulin (TBG), thyroxine binding prealbumin (TBPA), and albumin. Some physiologic actions of thyroid hormone include stimulation of metabolism, heart rate, protein synthesis, and carbohydrate metabolism in target tissues. The unbound (free) hormone is thought to be the physiologically active form while the protein bound fraction serves as a reservoir of available hormone. This complicates the determination of thyroid status because changes in the levels of binding proteins may lead to an increased total $T_4$ content in serum without affecting the level of free hormone (e.g. during pregnancy).

The production of $T_4$ is normally regulated by a feedback control loop which includes the hypothalamus and pituitary gland. In response to a lack of circulating $T_4$, the hypothalamus stimulates the pituitary gland to produce TSH. TSH in turn stimulates the production of $T_4$ by the thyroid gland. When circulating $T_4$ levels are adequate, the hypothalamus dictates that TSH production and thus, $T_4$ production decrease. Disruption of the feedback control loop in the hypothalamic-pituitary-thyroid axis leads to non-specific symptoms which can be diagnosed and effectively treated with the aid of laboratory tests. Primary hypothyroidism occurs due to destruction of the thyroid gland itself and results in decreased availability of $T_4$ to tissues. Failure of the pituitary to produce TSH also leads to hypothyroidism. Primary hyperthyroidism (an oversupply of $T_4$ to tissues) occurs due to excessive activity of the gland. Overproduction of TSH also leads to hyperthyroidism. Diagnostic tests aid in the detection of thyroid disease, in determining its mechanism, and in following its treatment.

From the discussion above, it is clear that a full understanding of thyroid function requires accurate assessments of the amounts of $T_3$, $T_4$ and TSH. In carrying out immunoassay procedures for determining concentrations of these thyroid analytes, a common practice is to use a family of controlled formulation solutions, hereinafter called standard or calibration solutions, each of which contains accurately predetermined quantities or concentrations of $T_4$, free $T_4$, $T_3$, free $T_3$, and TSH. Concentrations that are substantially lower and higher than normal are generally employed. Since the immunoassay procedures are normally designed to analyze serum samples, it is preferred that the calibration solutions be formulated using a matrix that is identical to or bioactively equivalent to serum. Human serum has typically been used as starting material for calibration solutions, however, the techniques used for stripping away endogenous thyroxine are known to produce process artifacts and wide lot-to-lot variations making it difficult to manufacture these solutions reproducibly. An additional disadvantage of calibration solutions containing human serum is that they cannot be stored for longer periods since serum contains many labile components which negatively affect the stability of the product. For this reason calibration materials are often provided in a dry state (lyophilized), however, inaccurate rehydration of these materials commonly leads to inaccurate calibration measures.

Liquid calibration solutions avoid the possibility of inaccurate rehydration of lyophilized calibration materials. Thus, there is a commercial advantage to providing liquid-stable materials which require no preparation by the end user. However, liquid calibration solutions must contain stabilizers and preservatives that act to increase the useful life and ensure against contaminants. Such reagents are known in the industry. However, the requirements placed on the formulation chemist to produce a combination of matrix, analyte, and preservative that are compatible with the analytical system, which can contain the desired concentrations of all desired analytes, and at the same time are able to maintain stability are known to be quite restrictive. Consequently, in practice, as many as five different calibration solutions may be required to support calibration protocols for $T_3$, free $T_3$, $T_4$, free $T_4$ and TSH. This imposes undesirable production expenses by the manufacturer as well as increased inventory and handling expenses by the clinical laboratory.

U.S. Pat. No. 5,342,788 discloses a serum-free standard solution containing TBG, albumin, and buffer. When $T_4$ or $T_3$ is added to this solution an equilibrium is established between bound and free hormone resembling that observed in human serum. Stability of the synthetic standard solution was superior to a solution based in human serum and furthermore, bovine TBG afforded superior stability than TBG derived from human serum.

A remaining shortcoming in the industry involves the addition of multiple thyroid-related analytes within a single liquid calibration solution for use in determination of thyroid function so as to increase flexibility in use as well as reduce production and inventory requirements. However, experience has shown that the simple addition of multiple analytes plus various anti-microbial agents within a single calibration solution would be expected to interfere with the analytical measurement of the other analytes in a sample or to even adversely affect the stability of another analyte in the solution. Accordingly, it was an object of the present invention to provide a single, stabilized calibration solution which included known amounts of $T_3$, $T_4$, free $T_4$, free $T_3$, and TSH so that the advantages of having a multi-analyte calibration solution could be realized over an extended period of time.

SUMMARY OF THE INVENTION

The present invention is based upon the discovery that a physiologic equilibrium of bound and free thyroid hormones can be established in a single liquid standard or calibration solution containing only albumin as a binding protein without the expected requirement for inclusion of TBG. Consequently, a calibration solution can be formulated simultaneously with specific amounts of triiodothyronine ($T_3$) in combination with specific amounts of thyroxine ($T_4$), which dictate levels of free $T_3$ and free $T_4$, respectively. In an alternate embodiment of this invention, purified TSH is also added to this thyroid hormone calibration solution even though TSH does not circulate in such a bound/free equilibrium so that a multiple-analyte assay calibration protocol may be accomplished using the single calibration solution. Unexpectedly, the presence of each one of the analytes has no adverse effect on the utility of the calibration solution in measuring the other analytes nor on the stability of the solution as a whole. In addition, an extended period of usage or stability of the calibration solution is achieved by including a combination of anti-microbial agents demonstrated to be active against bacteria and fungi and which do not adversely affect the utility of the calibration solution.

DETAILED DESCRIPTION OF THE INVENTION

Figure 1:
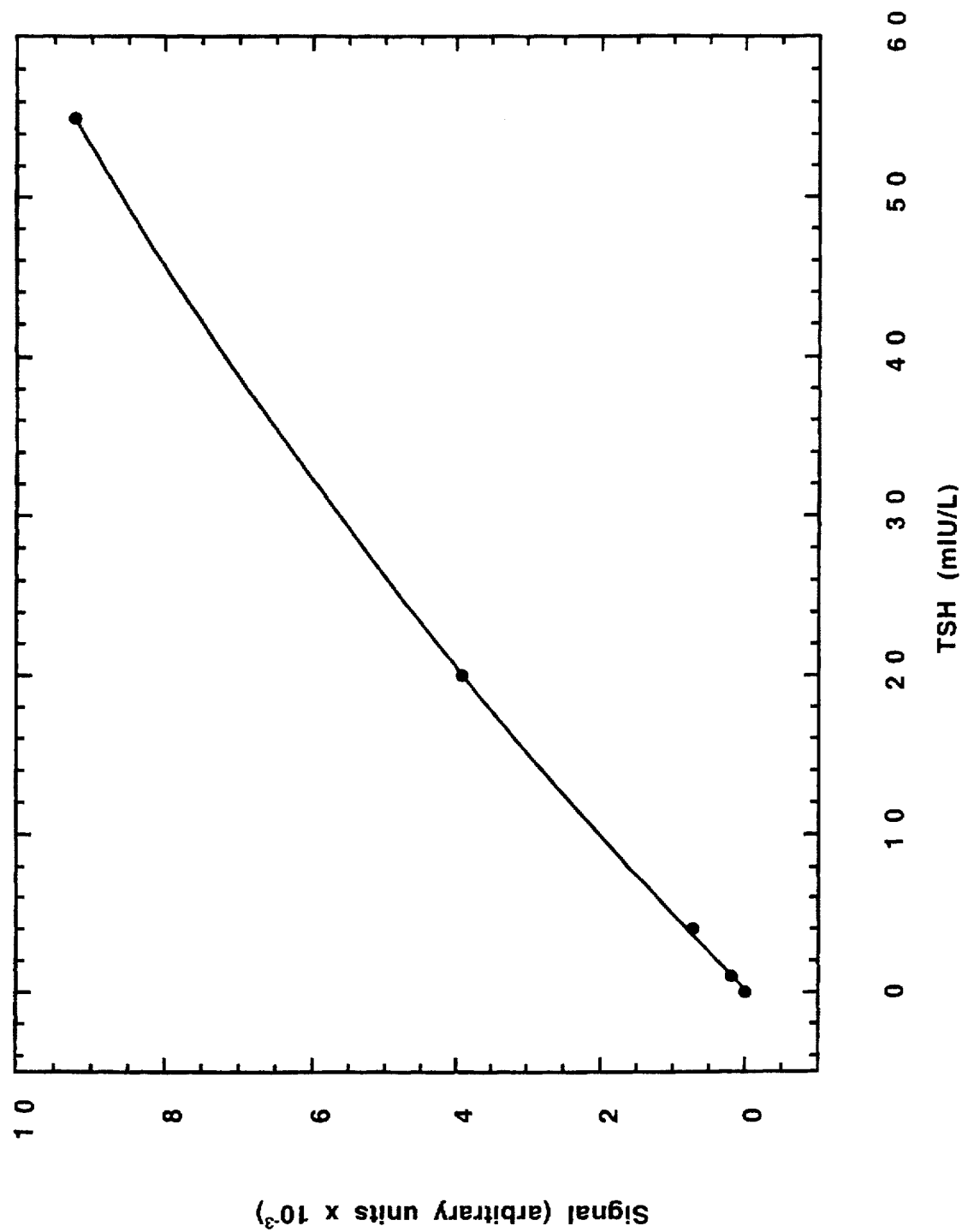
FIG. 1 is a calibration curve for a heterogeneous sandwich immunoassay for TSH using a calibration solution according to this invention.

Various methods are known for determining $T_4$, $T_3$, free $T_4$, free $T_3$, and TSH. Methods based on immunoassays are particularly useful in a routine clinical setting because automated platforms exist for the performance of these methods. Calibration of these automated platforms involves defining a mathematical relationship between the concentration of the analyte of interest and the detection signal generated. These relationships in immunoassays are commonly non linear such that a system requires multiple standard solutions to define the signal-analyte relationship.

As described herein and according to the invention, a standard solution, or calibration solution, with extended stability and being capable of simultaneous use in methods for determination of multiple thyroid-related analytes is provided which can be produced in a simple manner from easily obtainable starting materials. The calibration solution according to the present invention contains only serum albumin as a protein component. The protein serves as an acceptable binding reservoir for both $T_4$ and $T_3$ and an acceptable stabilizing milieu for TSH. Preferably, albumin from bovine serum is used as the albumin, although other sources of albumin are acceptable. Serum albumin is useful in a range between 40 g/L and 80 g/L which mimics the physiologic protein concentration of serum. Likewise, to mimic the ionic environment in serum, NaCl is added in a range between 100 and 200 mmoles/L solution. The amount of NaCl may vary depending on the sensitivity of the analytical system to ionic strength. If the analytical system is insensitive to ionic strength, NaCl addition may not be required. Likewise, to enhance the buffering capacity of the calibration solution, buffers which maintain pH in a range between 6.0 to 8.0 may be required. An example of such a buffer is HEPES (N-|2-hydroxyethyl|piperazine-N'-|2-ethanesulfonic add|). If the analytical system is insensitive to pH, the protein component of the matrix may supply all the buffering capacity that is required.

Subsequent to addition of protein, salt, and buffer, agents active against contaminating microbes are included in the calibration solution to achieve a desired amount of stabilization. These agents may consist of any number of compounds which are effective against bacteria and fungi, are inert in the analytical system, and are unreactive towards components of the matrix of the calibration solution and the specific analytes contained therein. In an exemplary embodiment, Polymyxin B, is added at a concentration of 0.02 g/L along with sodium pyrithione at a concentration of 0.2 g/L. At these concentrations, Polymyxin B is active mainly against bacteria and sodium pyrithione is active primarily against fungi. It is also useful to add a broad spectrum anti-microbial agent to reinforce the activities of the others. As an example, 0.1 g/L polyhexamethylene biguanide may be added. This particular combination of agents has been found to be very effective in providing a sterile environment for the calibration solution of the present invention for an extended period of six months or more as discussed hereinafter.

Subsequent to the preparation of the base matrix, the specific analytes of interest are added. Thyroxine is preferably added in a range between 0–500 µg/L, a range which covers the physiologically relevant concentrations found in human serum. Exemplary solutions are prepared with thyroxine content of 0, 17, 50, 100, and 400 µg/L (microgram per deciliter). In the presence of 60 g/L bovine serum albumin, these solutions dictate free thyroxine concentrations of approximately 0, 7, 20, 40, and 160 ng/L (nanogram per liter). Free $T_4$ measurements are poorly standardized in the diagnostic industry so free $T_4$ results may vary widely at a given concentration of $T_4$ depending on the analytical instrumentation.

Triiodothyronine is preferably used in a range between 0 and 12 µg/L solution since these concentrations span the physiologically relevant range of triiodothyronine concentrations found in human serum. Exemplary solutions are prepared with triiodothyronine content of 0, 1.0, 2.0, 4.0, and 9.0 µg/L . In the presence of 60 g/L bovine serum albumin, such solutions dictate free triiodothyronine content of approximately 0, 5, 11, 25, and 45 ng/L. Likewise, free $T_3$ measurements are poorly standardized in the diagnostic industry and the same degree of variation observed in free $T_4$ analyses may also be seen in free $T_3$ analyses at any given concentration of $T_3$ depending on the analytical instrumentation.

Thyroxine and triiodothyronine have the same structure independent of species so the source of these compounds may vary, also including synthetic material. TSH, however, varies according to animal species. Thus, for human diagnosis, TSH derived from humans or synthesized from the human gene sequence is required. TSH does not circulate in a bound/free equilibrium. The amount added is normally completely recovered without the addition of agents which release molecules from binding proteins. TSH is added to an exemplary solution in amounts of 0, 1, 4, 20, and 55 mIU/L (bioactivity units defined by World Health Organization standard material). Amounts of all analytes added are dictated by the relevant physiologic ranges and the requirements for defining a signal vs. concentration response for the specific analytical system.

Any combination of $T_4$, free $T_4$, $T_3$, free $T_3$, and TSH levels may be formulated depending on specific needs. The only limitations are the interdependence of total hormone levels and the free hormone levels. These cannot be adjusted independently.

This invention will be better understood by reference to the following example which is included here for purposes of exemplification and is not to be considered as limitative. Formulation techniques such as fluid handling, weighing, and mixing are done using standard laboratory equipment (e.g. pipettes, balances, and magnetic stirrers) and techniques known in the industry.

CALIBRATION SOLUTION

1. Preparation Of Matrix Preserved against Microbial Contamination.

a) Salt/buffer solution: 135 g of NaCl, 89.3 g of HEPES, and 97.5 g of Na-HEPES are dissolved in 15 L of water. Solute and solvent are mixed with a magnetic stirring apparatus until solute is completely dissolved. Mixing for 60 minutes at 25° C. is adequate. This buffer mixture is effective at maintaining the pH of the solution within a range of 7.0 to 8.0, preferably at 7.5.

b) Addition of antimicrobial agents: 3 g of sodium-pyrithione, 0.3 g of polymyxin B, and 1.5 g of polyhexamethylene biguanide are added sequentially to the salt/buffer solution and dissolved by stirring for 60 minutes at 25° C.

c) Addition of protein: To the preserved salt/buffer solution 900 g of bovine serum albumin is added and dissolved by mixing for 60 minutes at 25° C.

d) Following dissolution of the albumin the matrix is sterilized by filtration through a 0.2 micron filter. This solution is referred to hereinafter as a "preserved matrix".

2. Addition of analyte to the preserved matrix to generate a 5 level multi-analyte calibrator solution.

a) Level 1 consists only of preserved matrix and contains none of the analyte substances.

b) Four other solutions known as the "calibration solutions" (Levels 2–5) are formulated to contain analyte in specific concentrations from low concentrations (Level 2) to high concentrations (Level 5).

c) A 50 mg/L stock solution of $T_4$ is prepared by dissolution of $T_4$-sodium salt in 0.05N NaOH. Stock concentration is confirmed using the molar extinction coefficient of $T_4$ at 325 nm. Dilutions of this stock solution to 5 mg/L and 15 mg/L are prepared in 0.2 g/L bovine albumin solution and are referred to as "working dilutions". These working dilutions are prepared to allow accurate delivery to a specific level of the calibration solution and are formulated 100–200 times the desired final concentration to avoid large dilutions of the calibration solution upon their addition. The working dilutions are added to specified amounts of the preserved matrix to attain final concentrations of 100 and 400 µg/L of $T_4$ in levels 4 and 5, respectively. Levels 2 and 3 are prepared by dilution of level 4 with appropriate amounts of the preserved matrix to obtain concentrations of 17 µg/L and 50 µg/L, respectively. Levels 2–5 are mixed for 60 minutes at 25° C. These quantities of $T_4$ equilibrate between the bound and unbound state in the matrix to result in predictable unbound (free) $T_4$ concentrations of approximately 7, 20, 40, and 160 ng/L in levels 2, 3, 4, and 5, respectively.

d) A stock solution of purified human TSH is prepared by dissolving lyophilized TSH in cold (2°–8° C.) 9 g/L saline. Working dilutions containing 100, 400, 2000, and 4400 mIU/L of TSH are prepared in the preserved matrix. Levels 2, 3, 4, and 5 are formulated to contain 1.0, 4.0, 20.0, and 55.0 mIU/L TSH, respectively, using the appropriate working dilution. Levels 2–5, now containing $T_4$ and TSH, are mixed thoroughly for 60 minutes at 25° C.

e) Likewise, a 50 mg/L stock solution of $T_3$ (sodium salt) is prepared in 0.05N NaOH and its concentration confirmed by use of the known extinction coefficient of $T_3$ at 325 nm. Working dilutions are prepared in a 2 g/L bovine albumin solution containing 200, 400, 800, 1800 µg/L of T3 and used to formulate levels 2, 3, 4, and 5 containing 1.0, 2.0, 4.0, and 9.0 µg/L, respectively. Levels 2–5, now containing thyroxine, TSH, and $T_3$ are mixed for 60 minutes at 25° C. These quantities of $T_3$ equilibrate in the matrix to yield unbound (free) $T_3$ concentrations of approximately 0, 5, 11, 25, and 45 ng/L in levels 2, 3, 4, and 5, respectively.

g) No change in analyte concentrations (TSH, total $T_4$, free $T_4$, total $T_3$, and free $T_3$) are observed over a period of up to 5 days following the formulation stage. Mixing periods are designed to insure a homogenous product. Longer or shorter mixing periods and many modes of mixing are permissible.

Figure 2:
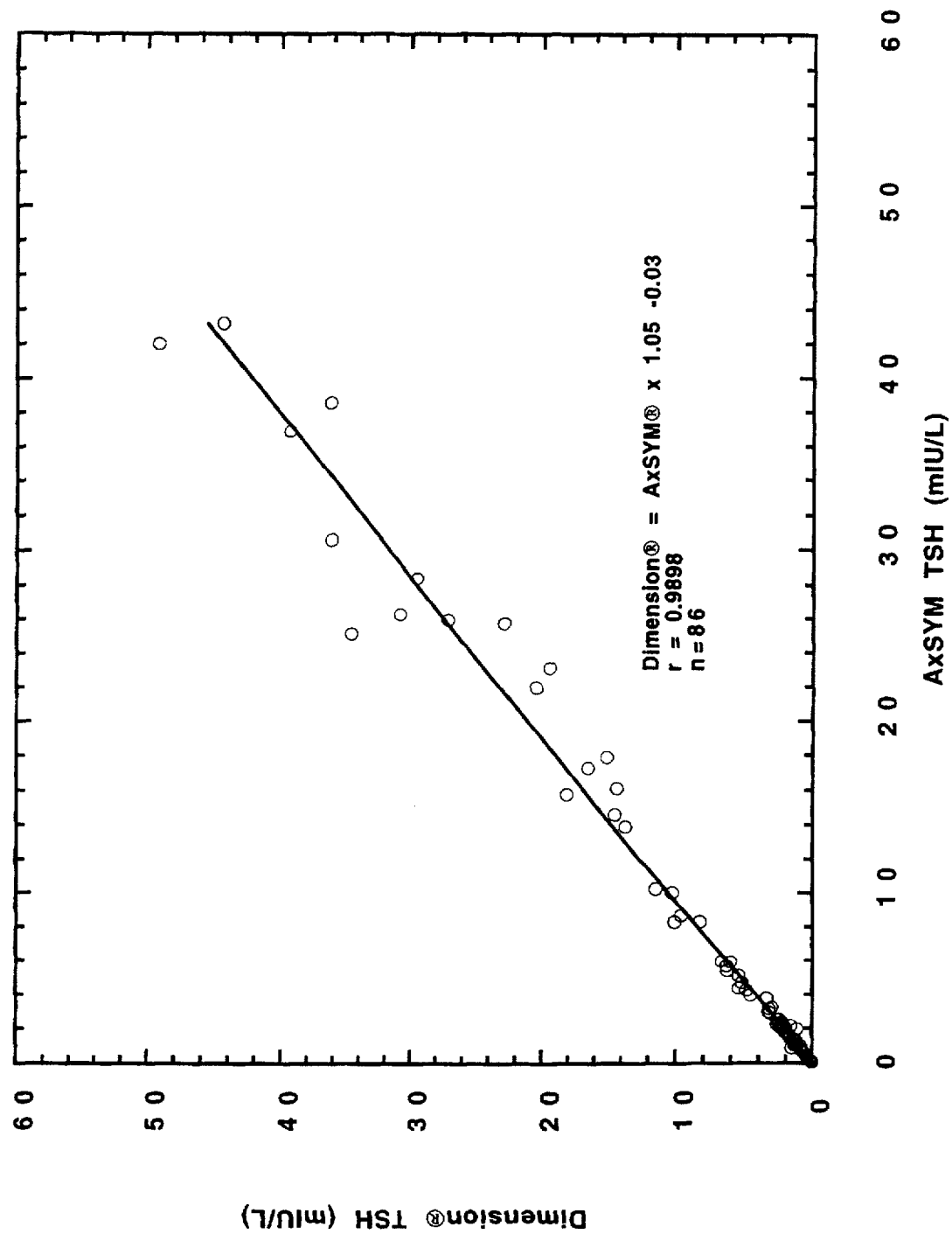
FIG. 2 compares the results of a TSH assay using a calibration solution made according to the present invention with results obtained using a known commercial system.

Large glycoprotein hormones like TSH are commonly measured by two-site "sandwich" immunoassay technology. FIG. 1 depicts a calibration curve for a heterogeneous sandwich immunoassay for TSH utilizing the calibration solution according to this invention on a Dimension® RxL Clinical Chemistry System, available from Dade International Inc., (Newark, Del.). FIG. 2 demonstrates the accuracy of the calibration solution in FIG. 1. Aliquots from 86 patient sera were measured on the Dimension® RxL Clinical Chemistry System calibrated with standard solution according to this invention and compared with an AXSYM® commercial analytical system calibrated with material and by instructions supplied by its manufacturer, Abbott Laboratories (Abbott Park, Ill.). The data show agreement between the two systems.

Figure 3:
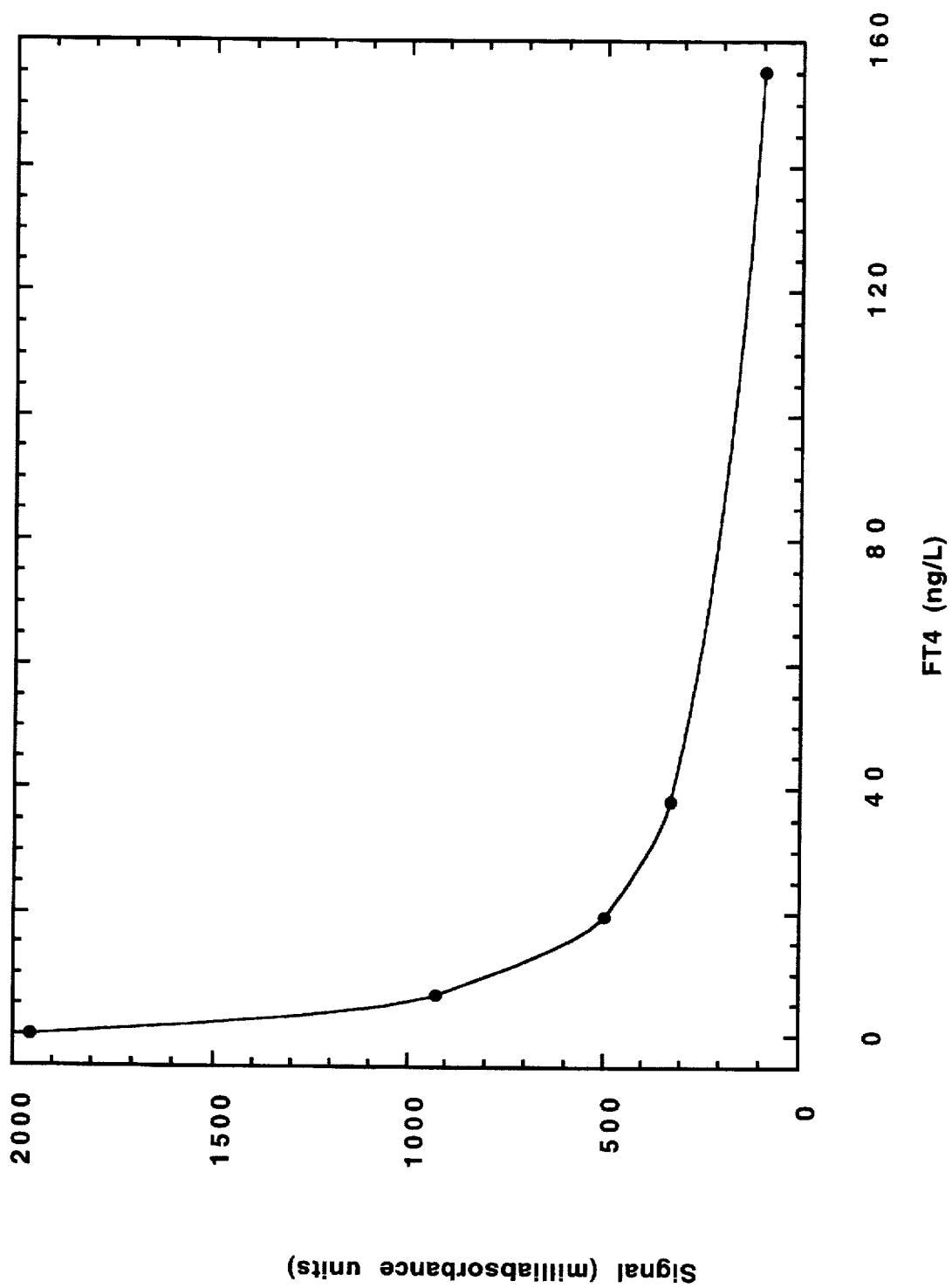
FIG. 3 is a calibration curve for a competitive hapten immunoassay for free $T_4$ using a calibration solution according to this invention.
Figure 4:
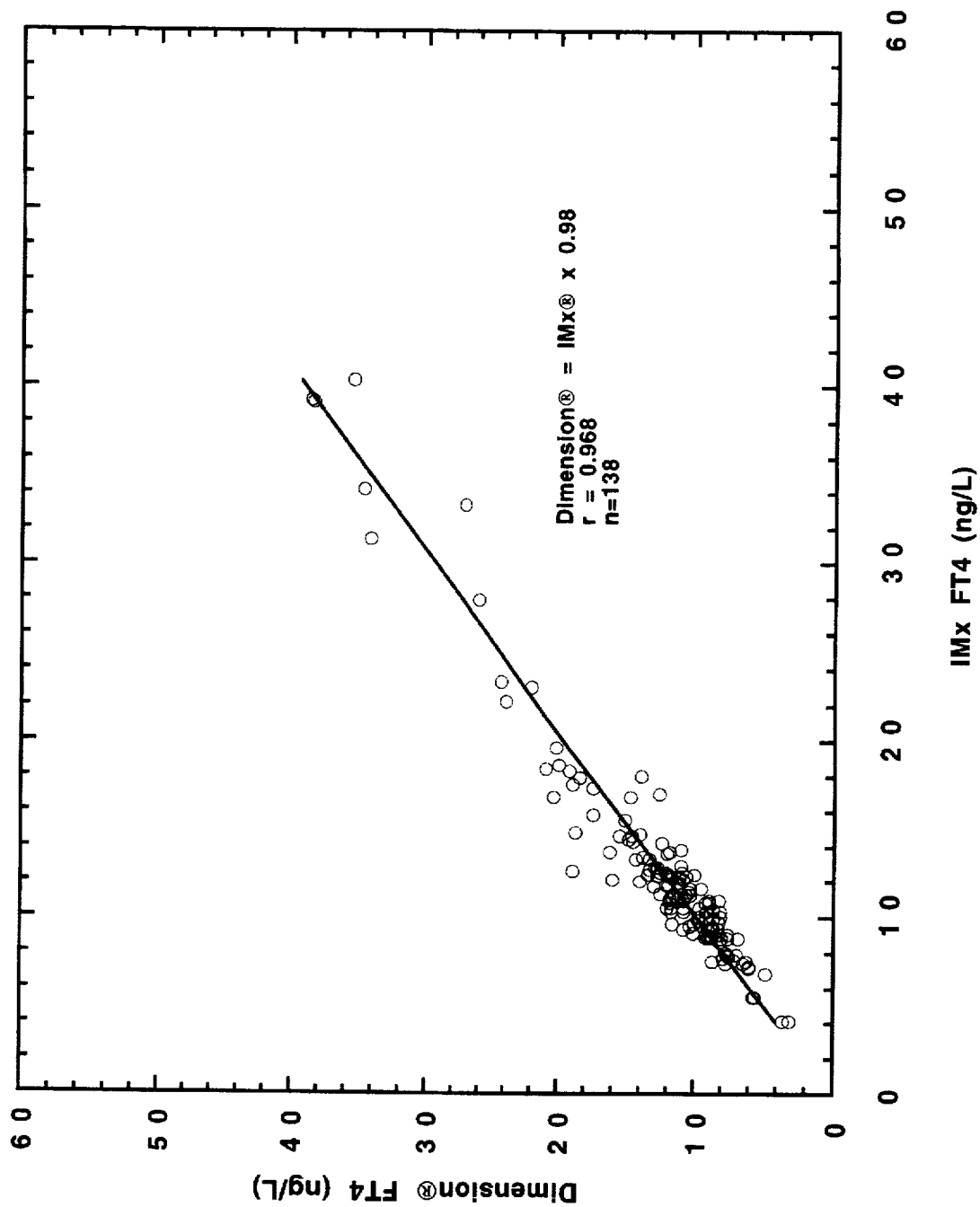
FIG. 4 compares the results of a free $T_4$ assay using a calibration solution made according to the present invention with results obtained using a known commercial system.

Molecules of smaller size and concentration such as free $T_4$, total $T_3$ and free $T_3$ are often determined by competitive hapten immunoassays and the signal resulting from such an assay is inversely proportional to the concentration of molecule. FIG. 3 depicts calibration curves for a competitive hapten immunoassay for free $T_4$ utilizing the same calibration solution of FIG. 1 according to this invention also using the Dimension® RxL Clinical Chemistry System. FIG. 4 demonstrates the accuracy of the calibration solution in FIG. 2. Aliquots from 138 patient sera were measured on the Dimension® RxL Clinical Chemistry System calibrated with standard solution according to this invention and compared with an IMx® commercial analytical system calibrated with material and by instructions supplied by its manufacturer, Abbott Laboratories. The data show agreement between the two systems.

Figure 5:
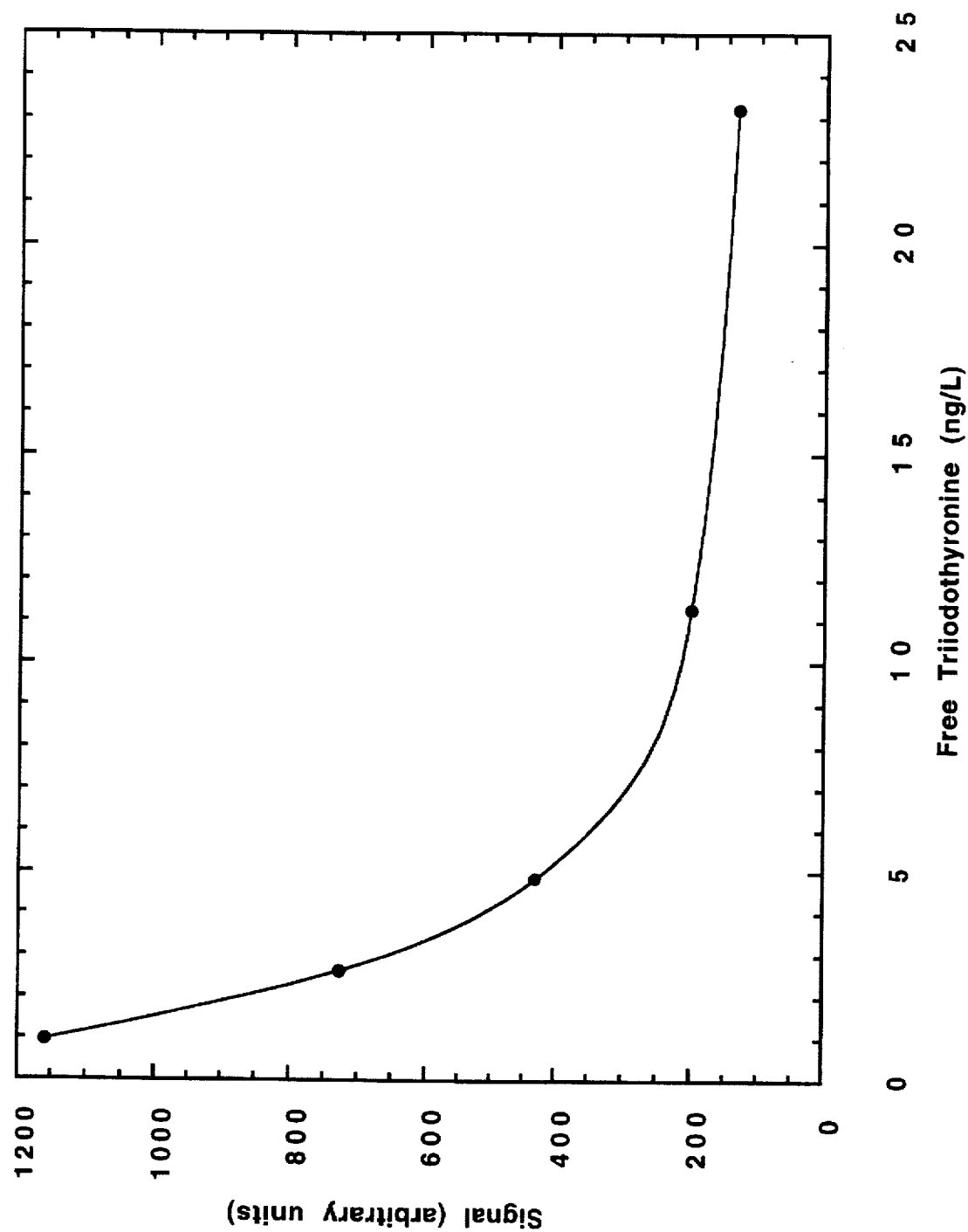
FIG. 5 depicts a calibration curve for free triiodothyronine assay using a calibration solution according to this invention.
Figure 6:
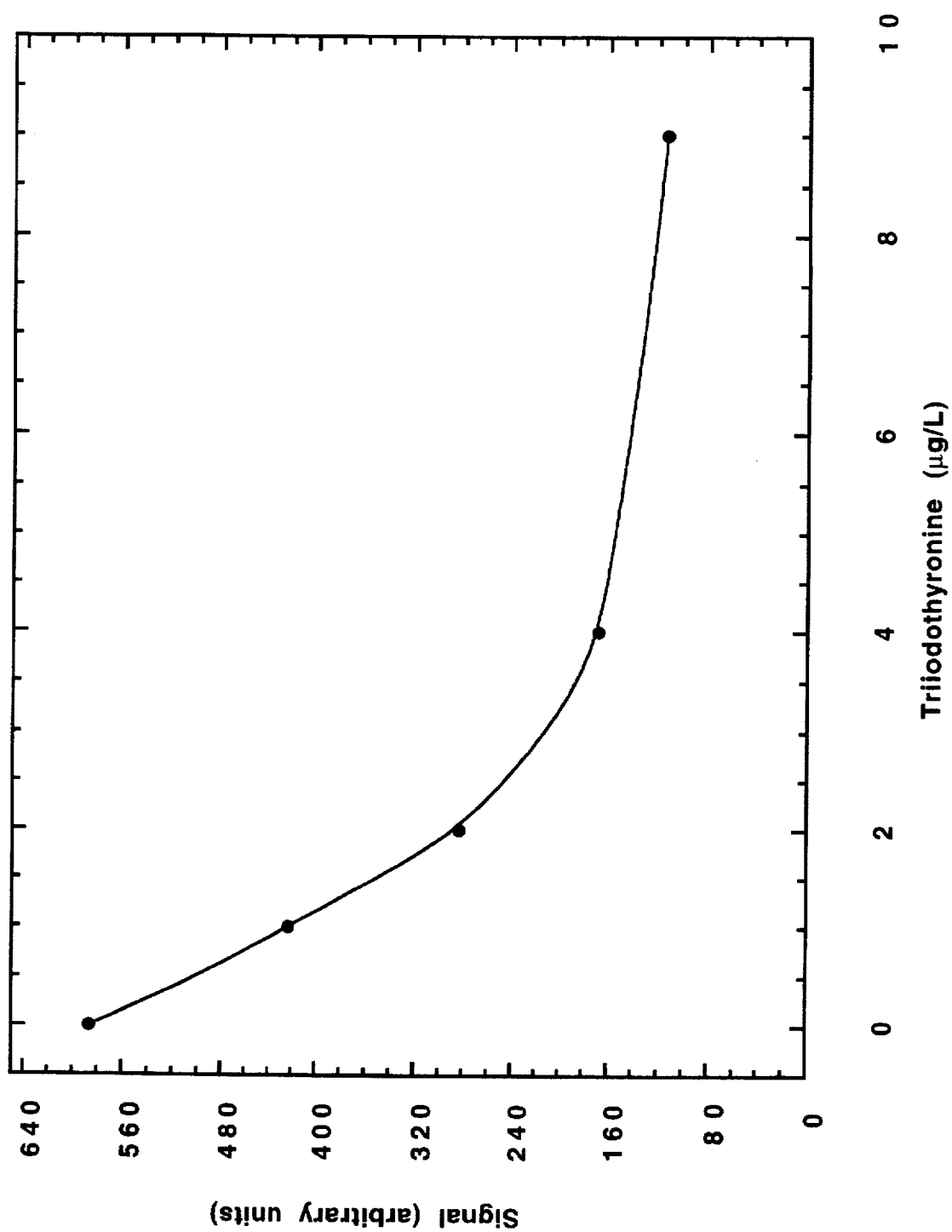
FIG. 6 depicts a calibration curve for total triiodothyronine assay using a calibration solution according to this invention.

Assays for free $T_3$ are performed in a similar fashion. FIG. 5 depicts a free $T_3$ calibration curve using a standard solution produced according to the present invention produced on an IMx® commercial system. A Total $T_3$ assay can be performed similarly to free hormone assays by use of an agent which releases $T_3$ from protein binding sites. FIG. 6 depicts a calibration curve for total $T_3$ using a competitive hapten immunoassay on the IMx® commercial analytical system.

Figure 7:
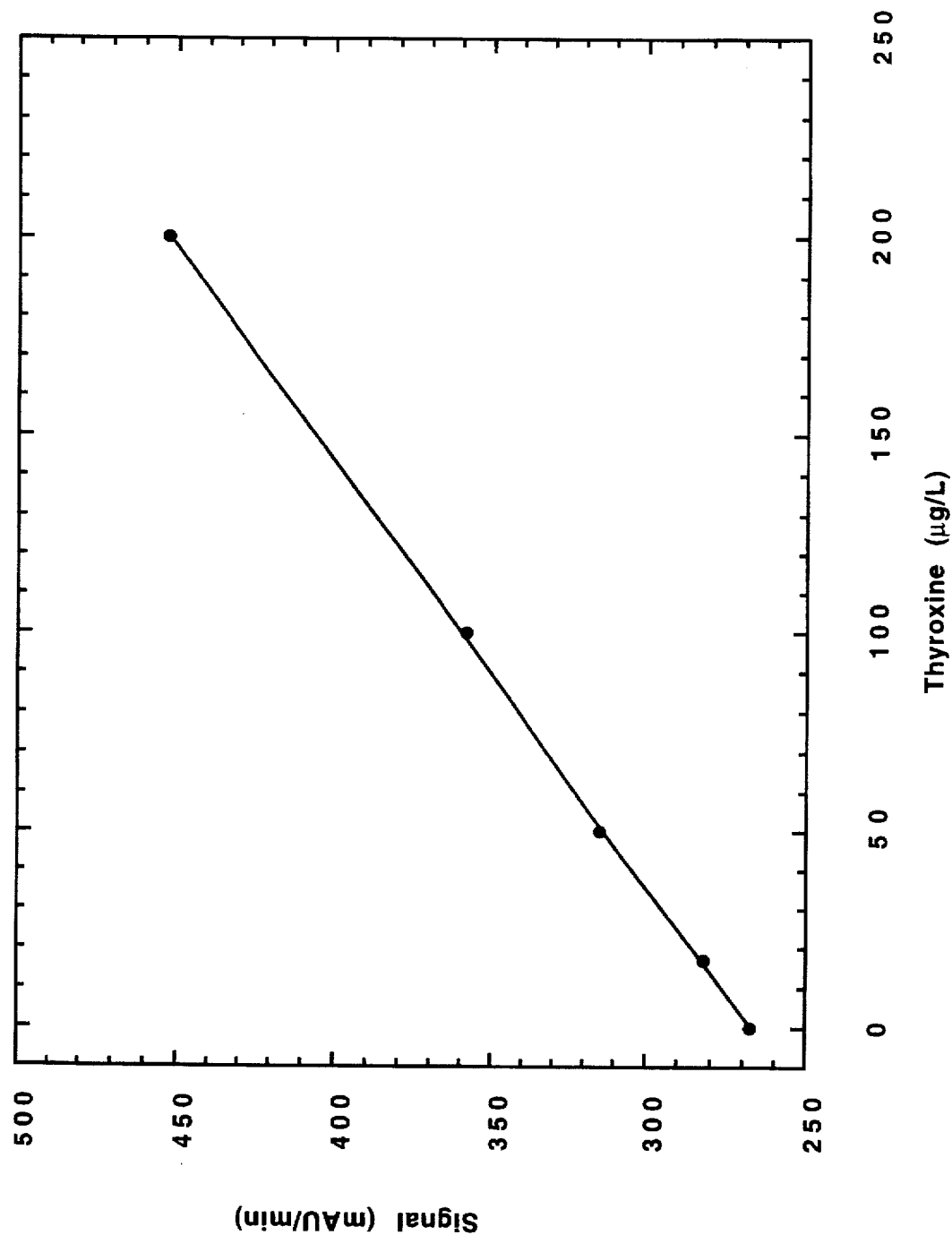
FIG. 7 depicts a calibration curve for a total L-thyroxine assay using a calibration solution according to this invention.

Unlike, TSH, free $T_4$, free $T_3$, and total $T_3$, total $T_4$ concentrations are large enough in human serum to be determined by immunoassay techniques which do not require a step to concentrate the molecule of interest. An example of a total $T_4$ calibration curve on the Dimension® commercial analytical system made using a calibration solution according to the present invention is shown in FIG. 7.

As illustrated in the Table below, all of the above calibration solutions have been found to be stable for six months or more when stored at 2°–8° C. A change in analyte value of 5% or more is normally considered unacceptable for commercial application of the calibration solutions. Stability of the analytes in the calibration solution was determined through measurement of these analytes by various commercial analytical systems. Samples of calibrator stored at 2°–8° C. were measured in parallel with samples stabilized by freezing at −70° C. Recovery of material is shown as the determined amount of the specific analyte in the material stored at 2°–80° C. divided by the determined amount of the specific analyte in the frozen material expressed as a percent. For all levels and analytes, virtually no change in analyte concentration at 2°–8° C. is detected.

TABLE

| Analyte | % of analyte recovered after 6 months storage at 2–8° C. in comparison to storage at −20° C. |
| --- | --- |
| Total Thyroxine | 99.5% |
| Free Thyroxine | 100.8% |
| Total Triiodothyronine | 100.4% |
| Free Triiodothyronine | 100.4% |
| Thyroid Stimulating Hormone | 99.8% |

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A standard solution useful in determining thyroid function comprising a single thyroid hormone binding protein in combination with known non-zero amounts of at least three analytes selected from the group consisting of total thyroxine, free thyroxine, total triiodothyronine, and free triiodothyronine, wherein said thyroid hormone binding protein is serum albumin.

2. The solution of claim 1 wherein the known amount of the total thyroxine is in a range between greater than 0 and 500 µg/L.

3. The solution of claim 1 wherein the known amount of the free thyroxine is in a range between greater than 0 and 160 ng/L.

4. The solution of claim 1 wherein the known amount of the total triiodothyronine is in a range between greater than 0 and 10 µg/L.

5. The solution of claim 1 wherein the known amount of the free triiodothyronine is in a range between greater than 0 and 50 ng/L.

6. The solution of claim 1 further comprising a known non-zero amount of thyroid stimulating hormone.

7. The solution of claim 6 wherein the known amount of the thyroid stimulating hormone is in a range between greater than 0 and 100 mIU/L.

8. The solution of claim 1 wherein the solution further comprises sufficient buffer to maintain pH in a range between 6–8.

9. The solution of claim 1 wherein the solution further comprises buffer within a range between 0 and 200 mmoles/L.

10. The solution of claim 1 wherein the solution further comprises NaCl in a range between 0 and 200 mmoles/L.

11. The solution of claim 1 further comprising a combination of anti-microbial agents effective in stabilizing the solution.

12. The solution of claim 11 wherein the anti-microbial agents are Na-pyrithione, Polymyxin B, and polyhexamethylene biguanide.

* * * * *

UNITED STATES PATENT AND TRADEMARK OFFICE
CERTIFICATE OF CORRECTION

PATENT NO. : 5,795,789
DATED : August 18, 1998
INVENTOR(S) : Dennis Jerome Dietzen It is certified that error appears in the above-identified patent and that said Letters Patent is hereby corrected as shown below:

Column 4, Line 5: Delete "add" and insert --acid--.

Column 6, Line 30: Delete "AXSYM®" and insert --AxSYM®--.

Column 7, Line 12: Delete "80°" and insert --8°--.

Signed and Sealed this

Twenty-fourth Day of November, 1998

Attest:

BRUCE LEHMAN

*Attesting Officer*   *Commissioner of Patents and Trademarks*